United States Patent
Englert et al.

(10) Patent No.: US 6,506,937 B2
(45) Date of Patent: *Jan. 14, 2003

(54) SUBSTITUTED BENZENESULFONYLUREAS AND -THIOUREAS-PROCESSES FOR THEIR PREPARATION AND THEIR USE AS PHARMACEUTICALS

(76) Inventors: Heinrich Englert, Hoechst Aktiengesellschaft, D-65926 Frankfurt am Main (DE); Dieter Mania, Hoechst Aktiengesellschaft, D-65926 Frankfurt am Main (DE); Jens Hartung, Hoechst Aktiengesellschaft, D-65926 Frankfurt am Main (DE); Heinz Gögelein, Hoechst Aktiengesellschaft, D-65926 Frankfurt am Main (DE); Joachim Kaiser, Hoechst Aktiengesellschaft, D-65926 Frankfurt am Main (DE); Wolfgang Linz, Hoechst Aktiengesellschaft, D-65926 Frankfurt am Main (DE); David Wettlaufer, Hoechst Aktiengesellschaft, D-65926 Frankfurt am Main (DE)

( * ) Notice: Subject to any disclaimer, the term of this patent is extended or adjusted under 35 U.S.C. 154(b) by 11 days.

This patent is subject to a terminal disclaimer.

(21) Appl. No.: 09/995,782

(22) Filed: Nov. 29, 2001

(65) Prior Publication Data

US 2002/0058838 A1 May 16, 2002

Related U.S. Application Data

(62) Division of application No. 09/490,078, filed on Jan. 24, 2000, now Pat. No. 6,335,467, which is a continuation of application No. 09/081,143, filed on May 19, 1998, now Pat. No. 6,090,981, which is a continuation of application No. 08/744,314, filed on Nov. 7, 1996, now Pat. No. 5,776,980, which is a continuation of application No. 08/707,103, filed on Sep. 3, 1996, now Pat. No. 5,698,596, which is a division of application No. 08/393,027, filed on Feb. 23, 1995, now Pat. No. 5,574,069, which is a continuation of application No. 08/198,048, filed on Feb. 18, 1994, now abandoned.

(30) Foreign Application Priority Data

Feb. 23, 1993 (DE) .......................... 43 05 450

(51) Int. Cl.[7] .................... C07C 311/16; C07C 311/58; C07C 335/42
(52) U.S. Cl. .......................... 564/86; 564/23; 564/39; 564/40; 564/41; 564/87; 564/88; 564/166; 564/170; 564/176; 564/177; 564/185; 564/186
(58) Field of Search ................. 564/166, 170, 564/176, 177, 185, 186, 86, 87, 88, 39, 40, 41

(56) References Cited

U.S. PATENT DOCUMENTS

| | | |
|---|---|---|
| 3,426,067 A | 2/1969 | Weber et al. |
| 3,917,690 A | 11/1975 | Weber et al. |
| 3,998,968 A | 12/1976 | Hitzel et al. |
| 5,215,985 A | 6/1993 | Murphy et al. |
| 5,574,069 A | 11/1996 | Englert et al. |
| 5,698,596 A * | 12/1997 | Englert et al. .............. 514/586 |
| 6,090,981 A * | 7/2000 | Englert et al. ................ 564/86 |
| 6,335,467 B1 | 1/2002 | Englert et al. |

FOREIGN PATENT DOCUMENTS

| | | |
|---|---|---|
| DE | 1518874 | 5/1970 |
| DE | 2413514 | 2/1976 |
| DE | 3011153 | 10/1981 |
| DE | 243821 | 3/1987 |
| GB | 1122820 | 8/1968 |
| GB | 1212695 | 11/1970 |

OTHER PUBLICATIONS

Linz et al., "Cardiovascular Effects of the Novel Potassium Channel Opener (3S,4R)–3–Hydroxy–2,2–dimethyl–4–(2–oxo–1–pyrrolidinyl)–6–phensylsulfonylchromane Hemihydrate," Arzneimittel–Forschung/Drug Research, 1992.

* cited by examiner

*Primary Examiner*—Shailendra Kumar

(57) ABSTRACT

Benzenesulfonylureas and -thioureas of the formula I

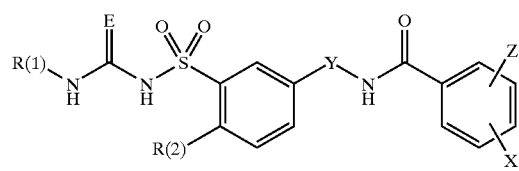

where R(1) is H or (fluoro)methyl, R(2) is H, Hal or (fluoro) (mercapto)alk(oxy)yl, E is O or S; Y is —[CR(3)$_2$]$_n$—, where R(3)=H or alkyl and n=1-4, X is H, Hal or alkyl and Z is Hal, $NO_3$ or alk(yl)oxy, are described.

The compounds I are used for treatment of disturbances in cardiac rhythm and prevention of sudden cardiac death caused by arrhythmia, and can therefore be used an antiarrhythmics. They are particularly suitable for those cases where arrhythmias are a consequence of a narrowing of a coronary vessel, such as angina pectoris or acute cardiac infarction.

11 Claims, No Drawings

SUBSTITUTED BENZENESULFONYLUREAS AND -THIOUREAS-PROCESSES FOR THEIR PREPARATION AND THEIR USE AS PHARMACEUTICALS

This is a division of application Ser. No. 09/490,078, filed Jan. 24, 2000, now U.S. Pat. No. 6,335,467, which is a continuation of application Ser. No. 09/081,143, filed May 19, 1998, now U.S. Pat. No. 6,090,981, which is a continuation of application Ser. No. 08/744,314, filed Nov. 7, 1996, now U.S. Pat. No. 5,776,980, which is a continuation of application Ser. No. 08/707,103, filed Sep. 3, 1996, now U.S. Pat. No. 5,698,596 which is a division of application Ser. No. 08/393,027, filed Feb. 23, 1995, now U.S. Pat. No. 5,574,069, which is a continuation of application Ser. No. 08/198,048, filed Feb. 18, 1994, abandoned, all of which are incorporated herein by reference.

DESCRIPTION

Substituted benzenesulfonylureas and -thioureas-processes for their preparation and their use as pharmaceuticals.

The invention relates to substituted benzenesulfonylureas and -thioureas I

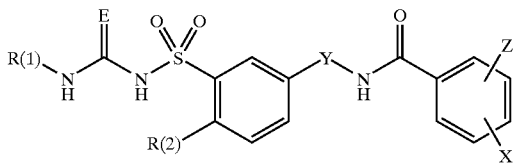

in which

R(1) is hydrogen, methyl, $CH_2F$, $CHF_2$ or trifluoromethyl,

R(2) is hydrogen, F, Cl, Br, I, $(C_1-C_6)$-alkyl, $(C_1-C_6)$-alkoxy, $(C_1-C_6)$-mercaptoalkyl, $(C_1-C_6)$-fluoroalkoxy or $(C_1-C_6)$-fluoroalkyl, E is oxygen or sulfur, Y is a hydrocarbon chain of the formula:

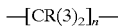

where $R(3)=H$ or $(C_1-C_2)$-alkyl and $n=1, 2, 3$ or $4$,

X is hydrogen, F, Cl, Br, I or $(C_1-C_6)$-alkyl and

Z is F, Cl, Br, I, $NO_2$, $(C_1-C_4)$-alkoxy or $(C_1-C_4)$-alkyl.

Unless stated otherwise, the term alkyl describes straight-chain, branched or cyclic saturated hydrocarbon radicals having one to six carbon atoms. The cycloalkyl radical can additionally carry alkyl or trifluoromethyl substituents. The term alkoxy represents an other substituent having a straight-chain, branched or cyclic saturated hydrocarbon radical of one to six carbon atoms. Fluoroalkyl describes a straight-chain, branched or cyclic saturated carbon skeleton of one to six carbon atoms, in which at least one hydrogen atom of the alkyl radical defined above is replaced by fluorine, but a maximum of perfluoro-substitution is reached. Fluoro-alkoxy is understood as meaning an other substituent which carries a fluoroalkyl radical according to the above definition. The elements fluorine, chlorine, bromine and iodine can be employed as the halogen substituent. Compounds having centers of chirality in the alkyl side chain Y furthermore may occur. In this case, both the individual antipodes in themselves and a mixture of the enantiomers or diastereomers in various ratios, as well as the associated meso compounds or mixtures of meso compounds, the enantiomers or diastereomers, belong to the invention.

Similar sulfonylureas are known from German Offenlegungs-schrift 2 413 514 and German Patent 1 518 874. DE-A 2 413 514 describes exclusively blood sugar-conditioning substances with p-substitution in the central phenyl group. There are no references to m-substitution or an amino substituent.

DE-C 1 518 874 describes hypoglycemic sulfonylureas of the formula

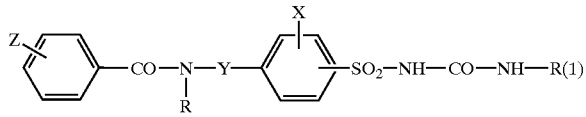

in which the central phenyl group can indeed also be m-substituted and trisubstituted, but in which R(1) can only be $(C_2-C_8)$-alkyl (in addition to many other meanings), and in which R(1) can never be a $C_1$ substituent or hydrogen.

The hypoglycemic action thereof in described in both patent publications. The prototype of such hypoglycemic sulfonylureas is glibenclamide, which is used therapeutically as an agent for the treatment of diabetes mellitus and is used in science as a much-regarded tool for researching so-called ATP-sensitive potassium channels. In addition to its hypoglycemic action, glibenclamide also has other actions which it has so far not yet been possible to employ therapeutically but which are all attributed to blockade precisely of those ATP-sensitive potassium channels. These include, in particular, an antifibrillatory action on the heart. However, simultaneous lowering of blood sugar would be undesirable or even dangerous during treatment of ventricular fibrillation or its preliminary stages, since it may deteriorate the condition of the patient further.

The object of the present invention was therefore to synthesize compounds which have a cardiac action which is equally as good an that of glibenclamide, but do not influence, or influence to a significantly lesser degree than glibenclamide, the blood sugar in cardioactive doses or concentrations.

Suitable test animals for detection of such actions are, for example, mice, rats, guineapigs, rabbits, dogs, monkeys or pigs.

The compounds I are used as medicament active compounds in human and veterinary medicine. They can furthermore be used as intermediate products for the preparation of other medicament active compounds.

Preferred compounds are those in which

R(1) is hydrogen, methyl or trifluoromethyl,

R(2) is hydrogen, $(C_1-C_6)$-alkyl, $(C_1-C_6)$-alkoxy, $(C_1-C_4)$-mercaptoalkyl, $(C_1-C_6)$-fluoroalkyl, $(C_1-C_6)$-fluoroalkoxy or F, Cl, Br or I, E is oxygen or sulfur, Y is a hydrocarbon chain of the formula $—[CR(3)_2]_n—$, where $R(3)=H$ or $C_1-C_2)$-alkyl and $n=1, 2, 3$ or $4$, X is hydrogen, F, Cl or $(C_1-C_4)$-alkyl and Z is nitro, F, Cl, $(C_1-C_4)$-alkyl or $(C_1-C_4)$-alkoxy.

Particularly preferred compounds I are those in which:

R(1) is hydrogen or methyl,

R(2) is $(C_1-C_6)$-alkyl or $(C_1-C_6)$-alkoxy,

E is oxygen or sulfur,

Y is a hydrocarbon chain of the formula: $—[R(3)_2]_n—$, where $R(3)=H$ or $(C_1-C_2)$-alkyl and $n=1, 2, 3$ or $4$, X is hydrogen, F, Cl or $(C_1-C_4)$-alkyl and Z is chlorine or fluorine, $(C_1-C_4)$-alkyl or $(C_1-C_4)$-alkoxy.

Especially preferred compounds I are those in which:

R(1) is hydrogen or methyl, and

R(2) is hydrogen, fluorine or chlorine,
E is oxygen or sulfur,
Y is a hydrocarbon chain of the formula: —[R(3)$_2$]$_n$—,
where R(3)=H or (C$_1$–C$_2$)-alkyl and n=1, 2, 3 or 4,
X is hydrogen, F, Cl or (C$_1$–C$_4$)-alkyl, and
Z is chlorine, fluorine, (C$_1$–C$_4$)-alkyl or (C$_1$–C$_4$)-alkoxy.

Compounds I which are likewise particularly preferred are those in which
R(1) is hydrogen or methyl,
R(2) is (C$_1$–C$_6$)-fluoroalkyl, (C$_1$–C$_6$)-fluoroalkoxy or (C$_1$–C$_6$)-mercaptoalkyl,
E is oxygen or sulfur,
Y is a hydrocarbon chain of the formula: —[CR(3)$_2$]$_n$—
where R(3)=H or (C$_1$–C$_2$)-alkyl and n=1, 2, 3 or 4,
X is hydrogen, F, Cl or (C$_1$–C$_4$)-alkyl and
Z is chlorine, fluorine, (C$_1$–C$_4$)-alkyl or (C$_1$–C$_4$)-alkoxy.

Particularly preferred compounds I are those in which:
R(1) is hydrogen or methyl,
R(2) is methoxy or methyl,
E is oxygen or sulfur,
Y is a hydrocarbon chain of the formula: —[CR(3)$_2$]$_n$—
where R(3)=H or methyl and n= 2 or 3,
X is hydrogen, F, Cl or (C$_1$–C$_3$)-alkyl and
Z is chlorine or fluorine, (C$_1$–C$_3$)-alkyl or (C$_1$–C$_3$)-alkoxy.

The compounds I of the present invention are useful medicaments for the treatment of disturbances in cardiac rhythm of widely varying origin and for prevention of sudden cardiac death caused by arrhythmia, and can therefore be used as antiarrhythmics. Examples of arrhythmic disturbances of the heart are supraventricular disturbances in rhythm, such as, for example, auricular tachycardia, auricular flutter or paroxysmal supraventricular disturbances in rhythm, or ventricular disturbances in rhythm, such as ventricular extrasystoles, but in particular life-threatening ventricular tachycardias or the particularly dangerous ventricular fibrillation. They are particularly suitable for those cases where arrhythmias are a consequence of a narrowing of a coronary vessel, such as occur, for example, with angina pectoris or during an acute cardiac infarction or as a chronic consequence of a cardiac infarction. They are therefore particularly suitable for prevention of sudden cardiac death in post-infarction patients. Other syndromes in which such disturbances in rhythm and/or sudden cardiac death caused by arrhythmia play a role are, for example, cardiac insufficiency or cardiac hypertrophy as a consequence of a chronically increased blood pressure.

The compounds I furthermore can positively influence a reduced contractility of the heart. This can be a disease-related decrease in cardiac contractility, for example in cases of cardiac insufficiency, or acute cases, such as cardiac failure under the effects of shock. In cases of a heart transplant, the heart likewise can resume its efficiency faster and more reliably after the operation has been performed. The same applies to operations on the heart which necessitate temporary stopping of cardiac activity by cardioplegic solutions, it being possible for the compounds to be used both for protection of the organs in the donor before and during removal, for protection of removed organs, for example during treatment with or storage thereof in physiological bath liquids, and during transfer into the recipient organism.

The invention furthermore relates to a process for the preparation of the compounds I, which comprises (a) reacting aromatic sulfonamides of the formula II or salts thereof of the formula III

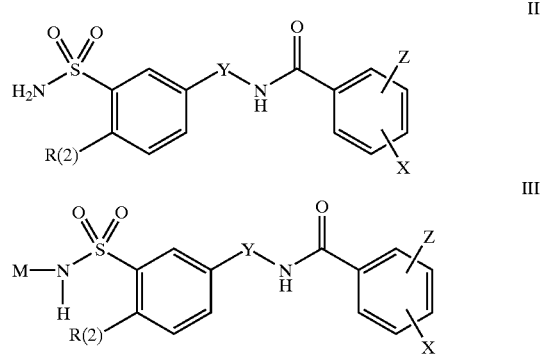

with R(1)-substituted isocyanates of the formula IV

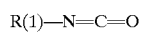

to give substituted benzenesulfonylureas Ia.

Possible cations M in the salts of the formula III are alkali metal and alkaline earth metal ions as well as tetraalkylammonium ions. As equivalent to the R(1)-substituted isocyanates IV, R(1)-substituted carbamic acid esters, R(1)-substituted carbamic acid halides or R(1)-substituted ureas can be employed.

(b) Unsubstituted benzenesulfonylureas Ia (R(1)=H)

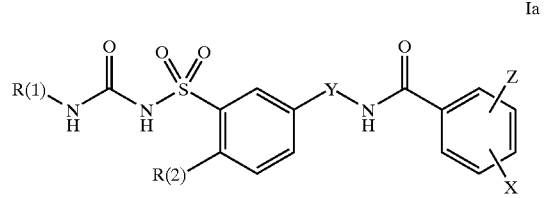

can be prepared by reactions of aromatic benzenesulfonamides of the formula II or their salts III with trialkylsilyl isocyanate or silicon tetraisocyanate and hydrolysis of the primary silicon-substituted benzenesulfonylureas. It is furthermore possible to prepare benzenesulfonamides II or their salts III by reaction with cyanogen halides and hydrolysis of the N-cyanosulfonamides primarily formed with mineral acids at temperatures of 0° C. to 100° C.

(c) Benzenesulfonylureas Ia

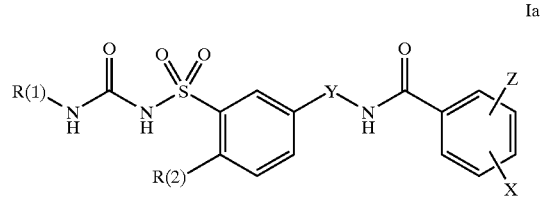

can be prepared from aromatic benzenesulfonamides II or their salts III and R(1)-substituted trichloroacetamides of the formula V

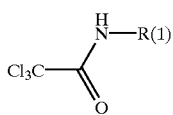

in the presence of a base in an inert solvent according to Synthesis 1987, 734–735 at temperatures of 25° C. to 150° C.

Suitable bases are, for example, alkali metal or alkaline earth metal hydroxides, hydrides, amides or also alcoholates, such as sodium hydroxide, potassium hydroxide, calcium hydroxide, sodium hydride, potassium hydride, calcium hydride, sodium amide, potassium amide, sodium methylate, sodium ethanolate, potassium methylate or potassium ethanolate. Suitable inert solvents are others, such as tetrahydrofuran, dioxane and ethylene glycol dimethyl ether (diglyme), nitriles, such as acetonitrile, amides, such as dimethylformamide (DMF) or N-methylpyrrolidone (NMP), phosphoric acid hexamethyltriamide, sulfoxides, such as dimethyl sulfoxide, sulfones, such as sulfolane, and hydrocarbons, such as benzene, toluene and xylenes. Furthermore, mixtures of these solvents with one another are also suitable.

(d) Benzenesulfonylthioureas Ib

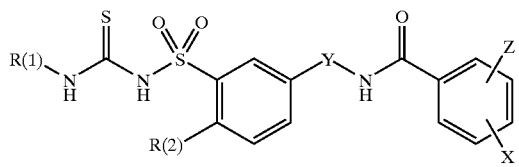

are prepared from benzenesulfonamides II and their salts III and R(1)-substituted thioisocyanates VI

Unsubstituted benzenesulfonylthioureas Ib (R(1)=H)

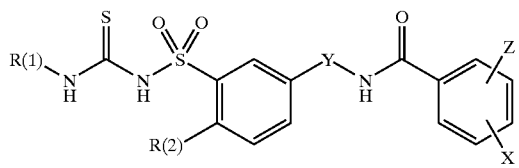

can be prepared by reactions of aromatic benzenesulfonamides II or their salts III with trimethlylsilyl isothiocyanate or silicon tetraisothiocyanate and hydrolysis of the silicon-substituted benzenesulfonylureas primarily formed.

It is furthermore possible to react aromatic benzenesulfonamides II or their salts III with benzoyl isothiocyanate and to react the benzoyl substituted benzenesulfonylthioureas intermediately formed with aqueous mineral acids to give Ib (R(1)=H). Similar processes are described in J. Med. Chem. 1992, 35, 1137–1144.

(a) Substituted benzenesulfonylureas of the formula Ia can be prepared by conversion reactions of benzenesulfonylthioureas of the structure Ib. The replacement of the sulfur atom by an oxygen atom in the correspondingly substituted benzenesulfonylthioureas Ib can be carried out, for example, with the aid of oxides or salts of heavy metals or also by using oxidizing agents, such as hydrogen peroxide, sodium peroxide or nitric acid. Thioureas can also be desulfurized by treatment with phosgene or phosphorus pentachloride. Chloroformic acid amidines or carbodiimides are obtained as intermediate compounds, which can be converted into the corresponding substituted benzenesulfonylureas Ia, for example, by hydrolysis or adding on of water. During desulfurization, isothioureas behave like thioureas and can accordingly likewise be used as starting substances for these reactions.

(f) Benzenesulfonylureas Ia can be prepared from benzenesulfonyl halides of the formula VII

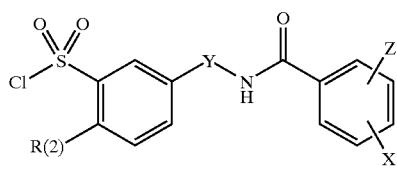

with R(1)-substituted ureas or R(1)-substituted bis (trialkylsilyl)ureas. The trialkylsilyl protective group can be removed from the resulting (trialkylsilyl) benzenesulfonylurea by standard methods. The sulfonic acid chlorides VII furthermore can be reacted with parabanic acids to give benzenesulfonylparabanic acids, hydrolysis of which with mineral acids gives the corresponding benzenesulfonylureas Ia.

(g) Benzenesulfonylureas Ia can be prepared by reactions of amines of the formula R(1)—N$_2$ with benzenesulfonyl isocyanates of the formula VIII

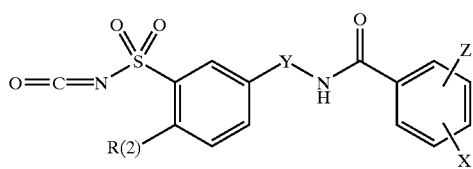

Amines R(1)—NH$_2$ can likewise be reacted with benzenesulfonylcarbamic acid esters or -carbamic acid halides or benzenesulfonylureas Ia (where R(1)=H) to give the compounds Ia.

(h) Benzenesulfonylthioureas Ib can be prepared by reactions of amines of the formula R(1)—NH$_2$ with benzenesulfonylisothiocyanates of the formula IX

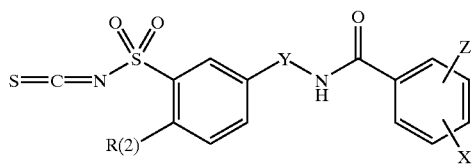

Amines R(1)—NH$_2$ likewise can be reacted with benzenesulfonylcarbamic acid thioesters or -carbamic acid thiohalides to give the compounds Ib.

(i) Correspondingly substituted benzenesulfenyl- or -sulfinylureas can be oxidized with oxidizing agents, such as hydrogen peroxide, sodium peroxide or nitric acid, to give benzenesulfonylureas Ia.

The compounds I and physiologically acceptable salts thereof are useful therapeutics which are suitable not only as antiarrhythmics but also as prophylactics for disturbances of the cardiovascular system, cardiac insufficiency, heart transplant or cerebral vascular diseases in humans or mammals (for example monkeys, dogs, mice, rats, rabbits, guineapigs and cats).

Physiologically acceptable salts of the compounds I are understood as meaning, in accordance with Remmington's Pharmaceutical Science, 17th edition, 1985, pages 14–18, compounds of the formula X

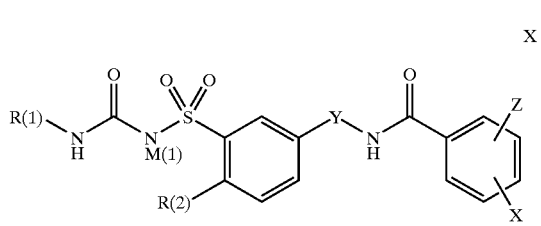

which can be prepared from non-toxic organic and inorganic bases and substituted benzenesulfonylureas I.

Preferred salts here are those in which M(1) in the formula X is sodium, potassium, rubidium, calcium or magnesium ions, and the acid addition products are basic amino acids, such as, for example, lysine or arginine.

The starting compounds for the synthesis processes mentioned for the benzenesulfonylureas I are prepared by methods which are known per se, such as are described in the literature (for example in the standard works, such as Houben-Weyl, Methoden der Organischen Chemie (Methods of Organic Chemistry), Georg Thieme Verlag, Stuttgart; Organic Reactions, John Wiley & Sons, Inc., New York; and in the abovementioned patent applications), and in particular under reaction conditions which are known and suitable for the reactions mentioned. It is also possible to use variants which are known per se but are not mentioned in more detail here. If desired, the starting substances can also be formed in situ such that they are not isolated from the reaction mixture but are immediately reacted further.

Equation 1

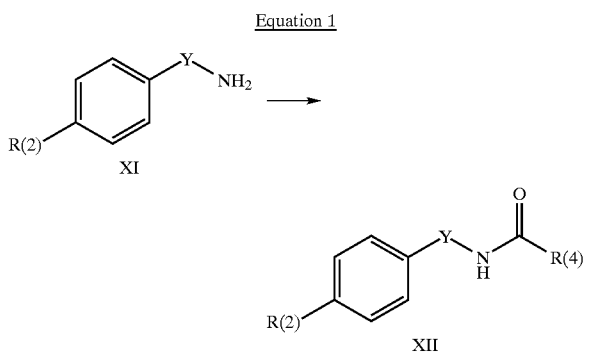

Thus, suitably substituted amines of the formula II can be acylated in accordance with equation 1 and subjected to halosulfonation. Suitable acylating agents for amino groups are expediently the alkyl esters, halides (for example chlorides or bromides) or anhydrides of carboxylic acids of the formula

R(4)—COB.

R(4) here is a trihalomethyl radical, a $(C_1-C_4)$-alkyl radical or a benzoic acid derivative. The benzoic acid derivatives here can be unsubstituted or substituted by one or two identical or different radicals X, Z. A possible substituent X is hydrogen, $(C_1-C_4)$-alkyl or halogen, and a substituent Z is hydrogen, halogen, $(C_1-C_4)$-alkyl, $(C_1-C_4)$-alkoxy or nitro.

B is a leaving group, such an halide, $(C_1-C_4)$-alkoxy, trihaloacetate or $(C_1-C_4)$-carboxylate. Examples here are acetic anhydride, trihaloacetic anhydride, acetyl halide, trihaloacetyl halide, propionyl chloride, isobutyryl bromide and chloride, benzoyl chloride, 5-chloro-2-methoxybenzoic acid chloride or anhydride and $(C_1-C_4)$-alkyl esters or 2,5-difluoro-benzoyl chloride. The syntheses of the compound XII are carried out with addition of a tertiary base, such as, for example, pyridine or trialkylamines, in the presence or absence of an inert solvent, it also being possible for a catalyst, such as, for example, dimethylaminopyridine, to be present. The reaction can be carried out at temperatures of about 0° C. to 160° C., preferably 20 to 150° C. The acyl group of the amines XI can be either a protective group or, in the case of the benzoic acid derivatives, part of the compound I. Suitable inert solvents are ethers, such as tetrahydrofuran, dioxane or glycol ethers, such as ethylene glycol monomethyl or monoethyl ether (methylglycol or ethylglycol) or ethylene glycol dimethyl ether (diglyme), ketones, such as acetone or butanone, nitriles, such as acetonitrile, amides, such as dimethylformamide (DMF) or N-methylpyrrolidone (NMP), phosphoric acid hexamethyltriamide, sulfoxides, such as dimethyl sulfoxide, chlorinated hydrocarbons, such as methylene chloride, chloroform, trichloroethylene, 1,2-dichloroethane or carbon tetrachloride, and hydrocarbons, such as benzene, toluene or xylenes. Furthermore, mixtures of these solvents with one another are also suitable.

Equation 2

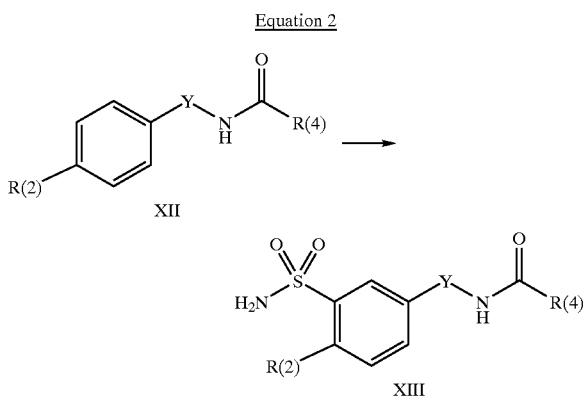

The amines XII acylated according to equation 1 can be converted into the sulfonamides XIII in a known manner in accordance with equation 2. The sulfonamides XIII are prepared by methods which are known per se, and in particular under reaction conditions which are known and suitable for the reactions mentioned. It is also possible to use variants which are known per se but are not mentioned in more detail here. If desired, the syntheses can be completed in one, two or more steps. Processes in which the acylated amino XII is converted into aromatic sulfonic acids and derivatives thereof, such as, for example, sulfonic acid halides, by electrophilic reagents in the presence or absence of inert solvents at temperatures of −10° C. to 120° C., preferably 0° C. to 100° C., are particularly preferred. For example, it in possible to carry out sulfonations with sulfuric acid or oleum, halosulfonations with halosulfonic acids, reactions with sulfuryl halides in the presence of anhydrous metal halides or thionyl halides in the presence of anhydrous metal halides, with subsequent oxidations carried out in a known manner, to give aromatic sulfonic acid chlorides. If sulfonic acids are the primary reaction products, these can be converted into sulfonic acid halides either directly or by treatment with tertiary amines, such as, for example, pyridine or trialkylamine, or with alkali metal or alkaline earth metal hydroxides or reagents which form this basic compound in situ, in a known manner by acid halides, such as, for example, phosphorus trihalides, phosphorus pentahalides, phosphorus oxychlorides, thionyl halides or oxalyl halides. The sulfonic acid derivatives are converted into sulfonamides in a manner known from the literature, and sulfonic acid chlorides are preferably reacted with aqueous ammonia in inert solvents at temperatures of 0° C. to 100° C. Aromatic sulfonamides furthermore can be synthesized by processes described in the literature from the acylated amines of the formula XII, prepared in accordance with equation 1, by reactions with organic alkali metal or alkaline earth metal reagents in inert solvents and under an inert gas atmosphere at temperatures of −100° C. to 50° C., preferably −100° C. to 30° C., with sulfur dioxide and subsequent thermal treatment with amidosulfonic acid.

If the acyl group functions as a protective group for the amine XII, it can then be eliminated with acids or bases after the sulfonamide XII has been prepared. The associated acid addition salt can be formed by cleavage with aqueous acids or acids in inert solvents. Possible acids for this reaction are, for example, sulfuric acid, hydrogen halide acids, such as hydrochloric acid or hydrobromic acid, phosphoric acids, such as orthophosphoric acid or polyphosphoric acid, sulfamic acid and furthermore organic acids, in particular aliphatic, alicyclic, araliphatic, aromatic or heterocyclic mono- or polybasic carboxylic, sulfonic or sulfuric acids, for example acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, phenylacetic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono and -disulfonic acids and laurylsulfuric acid. The cleavage of the acylated amine of the formula XIII with bases can also be carried out in aqueous or inert solvents. Suitable bases are, for example, alkali metal or alkaline earth metal hydroxides or also alcoholates in aqueous media, such as sodium hydroxide, potassium hydroxide, calcium hydroxide, sodium hydride, sodium methylate, sodium ethanolate, potassium methylate or potassium ethanolate.

The aromatic benzenesulfonamides of the formula II are prepared as mentioned above from the sulfonamide-substituted amines thus prepared or acid addition compounds thereof. Depending on the nature of the members R(1), R(2), R(3), E, X, Y and Z, one or other of the processes mentioned will be unsuitable for the preparation of compounds I, or at least necessitate measures for protection of active groups, in individual cases. Such cases, which occur relatively rarely, can be recognized easily by the expert, and there are no difficulties in successfully using one of the other synthesis routes described in such cases.

The compounds I can possess one or more chiral centers. They can therefore be obtained in their preparation as racemates or, if optically active starting substances are used, also in optically active form. If the compounds contain two or more chiral centers, they can be obtained in the synthesis an mixtures of racemates, from which the individual isomers can be isolated in the pure form, for example by recrystallization from inert solvents. If desired, resulting racemates can be separated mechanically or chemically into their enantiomers by methods which are known per se. Thus, diastereomers can be formed from the racemate by reaction with an optically active separating agent. Suitable separating agents for basic compounds are, for example, optically active acids, such as the R or R,R and S or S,S forms of tartaric acid, dibenzoyltartaric acid, diacetyltartaric acid, camphorsulfonic acid, mandelic acid, malic acid or lactic acid. Carbinols furthermore can be amidated with the aid of chiral acylating reagents, for example R- or S-α-methylbenzyl isocyanate, and then separated. The various forms of diastereomers can be separated in a known manner, for example by fractional crystallization, and the enantiomers of the formula I can be liberated in a manner which is known per se from the diastereomers. Enantiomer separations are also achieved by chromatography over optically active support materials.

The compounds I according to the invention and their physiologically acceptable salts can be used for the preparation of pharmaceutical formulations. In this context, they can be brought into a suitable dosage form together with at least one solid or liquid excipient or auxiliary, by themselves or in combination with other cardiovascular medicaments, such as, for example, calcium antagonists, NO donors or ACE inhibitors. These formulations can be used as medicaments in human or veterinary medicine. Possible excipients are organic or inorganic substances which are suitable for enteral (for example oral), parenteral, such as, for example, intravenous, administration or topical applications and with which the novel compounds do not react, for example water, vegetable oils, benzyl alcohols, polyethylene glycols, glycerol triacetate, gelatin, carbohydrates, such as lactose or starch, magnesium stearate, talc, lanolin and vaseline. Tablets, coated tablets, capsules, syrups, juices or drops are suitable in particular for oral use, solutions, preferably oily or aqueous solutions, and furthermore suspensions, emulsions or implants are suitable for rectal use, and ointments, creams, pastes, lotions, gels, sprays, foams, aerosols, solutions (for example in alcohols, such as ethanol or isopropanol, 1,2-propanediol or mixtures thereof with one another or with water) or powders are suitable for topical use. The novel compounds can also be lyophilized and the resulting lyophilizates can be used, for example, for the preparation of injection preparations. Liposomal preparations are also possible, in particular, for topical use. The [lacuna] comprise stabilizers and/or wetting agents, emulsifiers, salts and/or auxiliaries, such as lubricants, preservatives, stabilizers and/or wetting agents, emulsifiers, salts for influencing the osmotic pressure, buffer substances, dyestuffs and flavor and/or aroma substances. If desired, they can also comprise one or more other active compounds, for example one or more vitamins.

The dosages which are necessary for treatment of disturbances in cardiac rhythm using the compounds I depend on whether therapy is acute or prophylactic. A does range of about at least 0.01, preferably 0.1 mg, in particular 1 mg to not more than 100 mg, preferably 10 mg per kg and day is usually adequate if prophylaxis is carried out. A dose range of 1 to 10 mg per kg and day is particularly suitable. The dose here can be an oral or parenteral individual dose or divided into up to four individual doses. If acute cases of disturbances in cardiac rhythm are treated, for example in an intensive care ward, parenteral administration may be advantageous. A preferred dose range in critical situations can then be 10 to 100 mg, and can be administered, for example, as a continuous intravenous infusion.

In addition to the compounds described in the embodiment examples, the compounds I summarized in the following table can be obtained according to the invention:

(1) 2-Methoxy-5-chloro-N-{5-[1-sulfonylamino-N-(methylaminocarbonyl)-2-cyclopropoxyphenyl]-ethyl}-benzamide, (2) 2-Methoxy-5-chloro-N-{5-[1-sulfonylamino-N-(methylaminocarbonyl)-2-perfluoroethoxyphenyl]-ethyl}-benzamide, (3) 2-Methoxy-5-chloro-N-{5-[1-sulfonylamino-N-(methylaminocarbonyl)-2-(2-propoxy)phenyl]-ethyl}-benzamide, (4) 2-Methoxy-5-chloro-N-{5-[1-sulfonylamino-N-(methylaminocarbonyl)-2-(1-propoxy)phenyl]-ethyl}-benzamide, (5) 2-Methoxy-5-chloro-N-{5-[1-sulfonylamino-N-(trifluoremethylaminocarbonyl)-2-methoxyphenyl]-ethyl}-benzamide, (6) 2-Methoxy-5-chloro-N-{5-[1-sulfonylamino-N-(methylaminocarbonyl)-2-trifluoromethoxyphenyl]-ethyl}-benzamide, (7) 2-Ethoxy-5-chloro-N-{5-[1-sulfonylamino-N-(methylaminocarbonyl)-2-methoxyphenyl]-ethyl}-benzamide, (8) 2-(2-Propoxy)-5-chloro-N-{5-[1-sulfonylamino-N-(methylaminocarbonyl)-2-methoxyphenyl]-ethyl}-benzamide, (9) 2-(1-Propoxy)-5-chloro-N-{5-[1-sulfonylamino-N-(methylaminocarbonyl)-2-methoxyphenyl]-ethyl}-benzamide,

(10) 2-Cyclopropoxy-5-chloro-N-{5-[1-sulfonylamino-N-(methylaminocarbonyl)-2-methoxyphenyl]-ethyl}-benzamide,

(11) 2-Methoxy-5-fluoro-N-{5-[1-sulfonylamino-N-(methylaminocarbonyl)-2-ethylphenyl]-ethyl}-benzamide,

(12) 2-Methoxy-5-fluoro-N-{5-[1-sulfonylamino-N-(aminocarbonyl)-2-ethylphenyl]-ethyl}-benzamide,

(13) 2-Methoxy-5-chloro-N-{5-[1-sulfonylamino-N-(methylaminocarbonyl)-2-(1-propyl)phenyl]-ethyl}-benzamide,

(14) 2-Methoxy-5-chloro-N-{5-[1-sulfonylamino-N-(methylaminocarbonyl)-2-cyclopropylphenyl]-ethyl}-benzamide,

(15) 2-Methoxy-5-chloro-N-{5-[1-sulfonylamino-N-(aminocarbonyl)-2-cyclopropylphenyl]-ethyl}-benzamide,

(16) 2-Methoxy-5-chloro-N-{5-[1-sulfonylamino-N-(methylaminocarbonyl)-2-trifluoromethylphenyl]-ethyl}-benzamide,

(17) 2-Methoxy-5-fluoro-N-{5-[1-sulfonylamino-N-(methylaminocarbonyl)-2-cyclopropoxyphenyl]-[(1)-(R)-1-methylethyl]}-benzamide,

(18) 2-Methoxy-5-fluoro-N-{5-[1-sulfonylamino-N-(methylaminocarbonyl)-2-cyclopropoxyphenyl]-[(1)-(S)-1-methylethyl]}-benzamide,

(19) 2-Methoxy-5-fluoro-N-{5-[1-sulfonylamino-N-(methylaminocarbonyl)-2-cyclopropoxyphenyl]-[(2)-(R)-2-methylethyl]}-benzamide,

(20) 2-Methoxy-5-fluoro-N-{5-[1-sulfonylamino-N-(methylaminocarbonyl)-2-cyclopropoxyphenyl]-[(2)-(S)-2-methylethyl]}-benzamide,

(21) 2-Methoxy-5-chloro-N-{5-[1-sulfonylamino-N-(methylaminothiocarbonyl)-2-cyclopropoxyphenyl]-[(1)-(R)-1-methylethyl]}-benzamide,

(22) 2-Methoxy-5-fluoro-N-{5-[1-sulfonylamino-N-(methylaminothiocarbonyl)-2-cyclopropoxyphenyl]-[(1)-(S)-1-methylethyl]}-benzamide,

(23) 2-Methoxy-5-chloro-N-{5-[1-sulfonylamino-N-(methylaminothiocarbonyl)-2-cyclopropoxyphenyl]-[(2)-(R)-2-methylethyl]}-benzamide,

(24) 2-Methoxy-5-fluoro-N-{5-[1-sulfonylamino-N-(methylaminothiocarbonyl)-2-cyclopropoxyphenyl]-[(2)-(S)-2-methylethyl]}-benzamide,

(25) 2-Methoxy-5-fluoro-N-{5-[1-sulfonylamino-N-(methylaminocarbonyl)-2-methylphenyl]-[(1)-(R)-1-methylethyl]}-benzamide,

(26) 2-Methoxy-5-fluoro-N-{5-[1-sulfonylamino-N-(methylaminocarbonyl)-2-methylphenyl]-[(1)-(S)-1-methylethyl]}-benzamide,

(27) 2-Methoxy-5-fluoro-N-{5-[1-sulfonylamino-N-(methylaminocarbonyl)-2-methylphenyl]-[(2)-(R)-2-methylethyl]}-benzamide,

(28) 2-Methoxy-5-fluoro-N-{5-[1-sulfonylamino-N-(methylaminocarbonyl)-2-methylphenyl]-[(2)-(S)-2-methylethyl]}-benzamide,

(29) 2-Methoxy-5-chloro-N-{5-[1-sulfonylamino-N-(methylaminothiocarbonyl)-2-methylphenyl]-[(1)-(R)-1-methylethyl]}-benzamide,

(30) 2-Methoxy-5-fluoro-N-{5-[1-sulfonylamino-N-(methylaminothiocarbonyl)-2-methylphenyl]-[(1)-(S)-1-methylethyl]}-benzamide,

(31) 2-Methoxy-5-chloro-N-{5-[1-sulfonylamino-N-(methylaminothiocarbonyl)-2-methylphenyl]-[(2)-(R)-2-methylethyl]}-benzamide,

(32) 2-Methoxy-5-fluoro-N-{5-[1-sulfonylamino-N-(methylaminothiocarbonyl)-2-methylphenyl]-[(2)-(S)-2-methylethyl]}-benzamide,

(33) 2-Methoxy-5-fluoro-N-{5-[1-sulfonylamino-N-(methylaminocarbonyl)-2-methoxyphenyl]-[(1)-(R)-1-methylethyl]}-benzamide,

(34) 2-Methoxy-5-fluoro-N-{5-[1-sulfonylamino-N-(methylaminocarbonyl)-2-methoxyphenyl]-[(1)-(S)-1-methylethyl]}-benzamide,

(35) 2-Methoxy-5-fluoro-N-{5-[1-sulfonylamino-N-(methylaminocarbonyl)-2-methoxyphenyl]-[(2)-(R)-2-methylethyl]}-benzamide,

(36) 2-Methoxy-5-fluoro-N-{5-[1-sulfonylamino-N-(methylaminocarbonyl)-2-methoxyphenyl]-[(2)-(S)-2-methylethyl]}-benzamide,

(37) 2-Methoxy-5-chloro-N-{5-[1-sulfonylamino-N-(methylaminothiocarbonyl)-2-methoxyphenyl]-[(1)-(R)-1-methylethyl]}-benzamide,

(38) 2-Methoxy-5-fluoro-N-{5-[1-sulfonylamino-N-(methylaminothiocarbonyl)-2-methoxyphenyl]-[(1)-(S)-1-methylethyl]}-benzamide,

(39) 2-Methoxy-5-chloro-N-{5-[1-sulfonylamino-N-(methylaminothiocarbonyl)-2-methoxyphenyl]-[(2)-(R)-2-methylethyl]}-benzamide,

(40) 2-Methoxy-5-fluoro-N-{5-[1-sulfonylamino-N-(methylaminothiocarbonyl)-2-methoxyphenyl]-[(2)-(S)-2-methylethyl]}-benzamide,

(41) 2-Methoxy-5-chloro-N-{5-[1-sulfonylamino-N-(methylaminocarbonyl)-2-methoxyphenyl]-(3-propyl)}-benzamide.

(42) 2-Methoxy-5-chloro-N-{5-[1-sulfonylamino-N-(methylaminocarbonyl)-2-methoxyphenyl]-(4-butyl)}-benzamide,

(43) 2-Methoxy-5-fluoro-N-{5-[1-sulfonylamino-N-(methylaminothiocarbonyl)-2-methoxyphenyl]-(3-propyl)}-benzamide,

(44) 2-Methoxy-5-fluoro-N-{5-[1-sulfonylamino-N-(methylaminothiocarbonyl)-2-methoxyphenyl]-(4-butyl)}-benzamide.

EXAMPLE 1

2-Methoxy-5-chloro-N-{5-[1-sulfonylamino-N-(methylaminocarbonyl)-2-methoxyphenyl]-ethyl}-benzamide

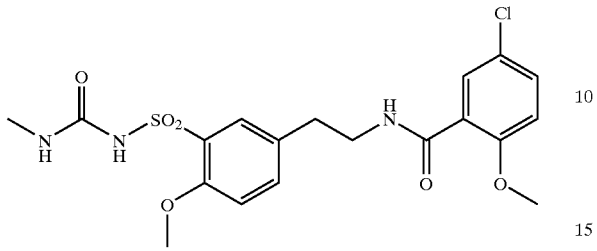

0.30 g (0.8 mmol) of 2-methoxy-5-chloro-N-[5-(1-sulfonylamino-2-methoxyphenyl)-ethyl]-benzamide is dissolved in 2 ml of dry dimethyl sulfoxide and, after addition of 0.9 g (2.23 mmol) of sodium hydroxide and 0.15 g (0.8 mmol) of N-methyltrichloroacetamide, the mixture is heated at 80° C. for 3 hours. The cool reaction mixture is poured onto aqueous, dilute hydrochloric acid and the precipitate is filtered off with suction and recrystallized from acetonitrile. 2-Methoxy-5-chloro-N-{5-[1-sulfonylamino-N-(methylaminocarbonyl)-2-methoxyphenyl]-ethyl}-benzamide has a melting point of 201–203° C.

Preparation of the Starting Compounds 1.51 g (10.0 mmol) of 4-methoxy-β-phenylethylamine are dissolved in 40 ml of pyridine, a spatula-tip of dimethylaminopyridine is added and a solution of 2.15 g (10.5 mmol) of 2-methoxy-5-chlorobenzoyl chloride is added. The reaction mixture is poured onto cold dilute hydrochloric acid and the product which has precipitated is filtered off with suction and dried. 4-Methoxy-β-ethyl-(2-methoxy-5-chlorobenzamide) is obtained as colorless crystals of melting point 83–84° C. The benzamide thus obtained is introduced into cold chlorosulfonic acid. When the reaction is complete, the reaction mixture is poured onto ice and the precipitate is filtered off with suction (melting point of the sulfonic acid chloride: 140–141° C.) and dissolved in acetone. Excess, concentrated, aqueous ammonia is added to this solution and, when the exothermic reaction has subsided, the mixture in concentrated to one third of the original volume. 2-Methoxy-5-chloro-N-[5-(1-sulfonylamino-2-methoxyphenyl)-ethyl]-benzamide is obtained as colorless crystals of melting point 220–222° C.

EXAMPLE 2

2-Methoxy-N-{5-[1-sulfonylamino-N-(methylaminocarbonyl)-2-methoxyphenyl]-ethyl}-benzamide

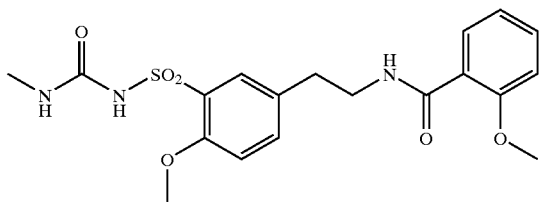

0.30 g (6.6 mmol) of 2-methoxy-5-chloro-N-{5-[1-sulfonylamino-N-(methylaminocarbonyl)-2-methoxyphenyl]-ethyl}-benzamide is dissolved in 20 ml of methanol and the solution is stirred with 0.1 g of 10 percent strength palladium-on-active charcoal in a hydrogen atmosphere for 24 hours. The catalyst is filtered off, the solvent is removed and the colorless residue is recrystallized from acetonitrile. Melting point: 190–191° C.

EXAMPLE 3

2-Methoxy-5-chloro-N-{3-[1-sulfonylamino-N-(methylaminocarbonyl)phenyl]-ethyl}-benzamide

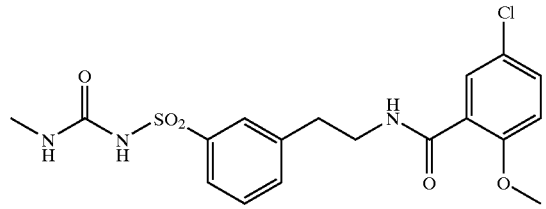

0.40 g (1.0 mmol) of 2-methoxy-3-chloro-N-[3-(1-sulfonylaminophenyl)-ethyl]-benzamide is dissolved in 5 ml of dry DMF and, after addition of 0.10 g (2.5 mmol) of sodium hydroxide and 0.27 g (1.2 mmol) of N-methyltrichloroacetamide, the mixture is heated at 80° C. for 2 hours. The cool reaction mixture in poured onto aqueous, dilute hydrochloric acid and the precipitate in filtered off with suction and recrystallized from acetonitrile. 2-Methoxy-5-chloro-N-{3-[1-sulfonylamino-N-(methylaminocarbonyl)phenyl]-ethyl}-benzamide has a melting point of 179–180° C.

Preparation of the Starting Compound 15.6 g (0.1 mol) of 2-(4-chlorophenyl)ethylamine are dissolved in 80 ml of tetrahydrofuran and 16.3 ml (0.15 mmol) of pyridine, and 21.2 ml (0.15 mol) of trifluoroacetic anhydride are added, while cooling. After 1 to 2 hours, the reaction mixture is poured onto ice and the product which has precipitated is filtered off with suction. This product is converted into the corresponding sulfonamide (melting point: 172–174° C.) as described in Example 1. Reduction of the chlorinated sulfonamide by means of hydrogen in the presence of 10 percent strength palladium-on-active charcoal in methanol as the solvent gives 2-(1-sulfonylaminophenyl)ethyltrifluoroacetamide, which is converted into the corresponding amino hydrochloride by heating in aqueous hydrochloric acid. The amine hydrochloride in reacted with 2-methoxy-5-chlorobenzoyl chloride and triethylamine in dimethylformamide and in the presence of dimethylaminopyridine to give 2-methoxy-5-chloro-N-[3-(1-sulfonylaminophenyl)-ethyl]-benzamide. Melting point: 196–198° C.

EXAMPLE 4

2-Methoxy-5-chloro-N-{5-[1-sulfonylamino-N-(methylaminocarbonyl)-2-methylphenyl]-ethyl}-benzamide

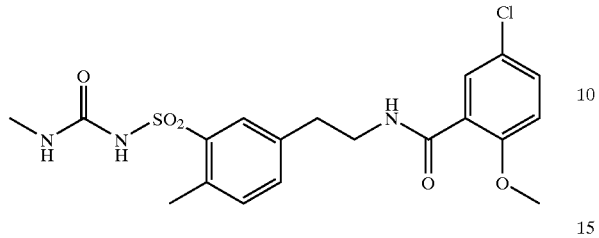

2-Methoxy-5-chloro-N-{5-[1-sulfonylamino-N-(methylaminocarbonyl)-2-methylphenyl]-ethyl}-benzamide is prepared from p-tolyl-β-ethylamine by a procedure analogous to that described in Example 1. Melting point: 192–193° C.

EXAMPLE 5

2-Methoxy-5-chloro-N-{5-[1-sulfonylamino-N-(methylaminocarbonyl)-2-(2-propyl)-phenyl]-ethyl}-benzamide

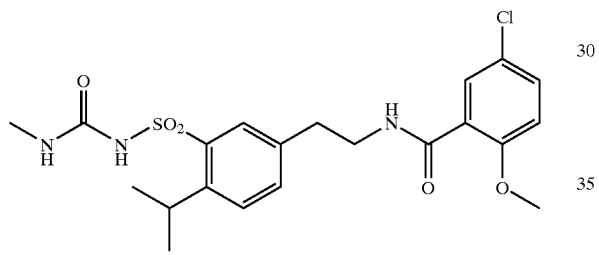

2-Methoxy-5-chloro-N-{5-[1-sulfonylamino-N-(methylaminocarbonyl)-2-(2-propyl)-phenyl]-ethyl}-benzamide can be prepared from 2-[2-(propyl)phenyl]ethylamine analogously to Example 1 and has a melting point of 190° C. Chlorosulfonation of 4-cumyl-β-ethyl-(2-methoxy-5-chlorobenzamide) gives isomeric sulfonic acid chlorides which are separated at the following stage of the sulfonamide by crystallization from ethyl acetate.

EXAMPLE 6

2,5-Difluoro-N-{5-[1-sulfonylamino-N-(methylaminocarbonyl)-2-methylphenyl]-ethyl}-benzamide

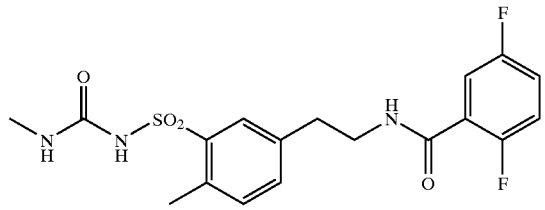

2-(1-Sulfonylamino-2-methylphenyl)ethylamine hydrochloride, which is synthesized in accordance with Example 4 from 2-(p-tolyl)ethylamine, can be converted into 2,5-difluoro-N-{5-[1-sulfonylamino-N-(methylaminocarbonyl)-2-methylphenyl]-ethyl}-benzamide, melting point: 196–198° C., as described first with 2,5-difluorobenzoyl chloride and then with N-methyltrichloroacetamide and sodium hydroxide in dimethyl sulfoxide.

EXAMPLE 7

2-Nitro-5-chloro-N-{5-[1-sulfonylamino-N-(methylaminocarbonyl)-2-methylphenyl]-ethyl}-benzamide

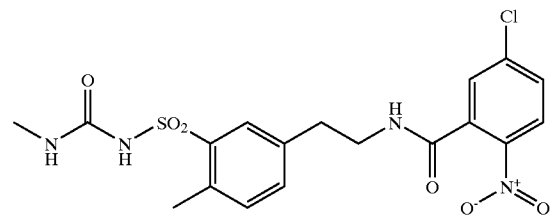

2-Nitro-5-chloro-N-{5-[1-sulfonylamino-N-(methylaminocarbonyl)-2-methylphenyl]-ethyl}-benzamide, which melts at between 165 and 170° C., with decomposition, can be prepared analogously to Example 6.

EXAMPLE 8

2-Methoxy-5-chloro-N-[1-Sulfonylamino-N-(methylaminocarbonyl)-2-methoxybenzyl]-benzamide

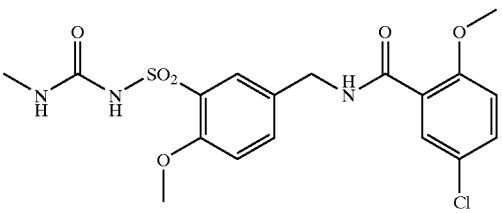

4-Methoxybenzylamine in converted into 2-methoxy-5-chloro-N-[1-sulfonylamino-N-(methylaminocarbonyl)-2-methoxybenzyl]-benzamide as described in example 1. The compound is colorless and crystalline and melts in the temperature range of 206–210° C.

EXAMPLE 9

2-Methoxy-5-chloro-N-{5-[1-sulfonylamino-N-(aminocarbonyl)-2-methoxyphenyl]-ethyl}-benzamide

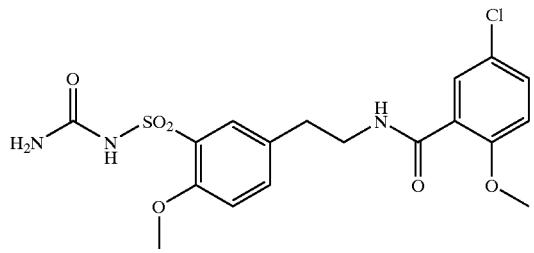

0.40 g (1.0 mmol) of 2-methoxy-5-chloro-N-[5-C1-sulfonylamino-2-methoxyphenyl)-ethyl]-benzamide from Example 1 is dissolved in 5 ml of acetonitrile, and 0.14 g (1.0 mol) of potassium carbonate and 1 ml of 1 molar cyanogen bromide solution in acetonitrile are added. After the mixture has been heated for several hours, 0.14 g of 2-methoxy-5-chloro-N-[5-(1-sulfonylamino-N-cyano-2-methoxyphenyl)-ethyl]-benzamide is isolated by column chromatography and is converted into 2-methoxy-5-chloro-N-{5-[1-sulfonylamino-N-(aminocarbonyl)-2-methoxyphenyl]-ethyl}-benzamide with cold, half-concentrated sulfuric acid. Melting point: 180–185° C.

EXAMPLE 10

2-Methoxy-5-chloro-N-{5-[1-sulfonylamino-N-(methylaminothiocarbonyl)-2-methoxyphenyl]-ethyl}-benzamide

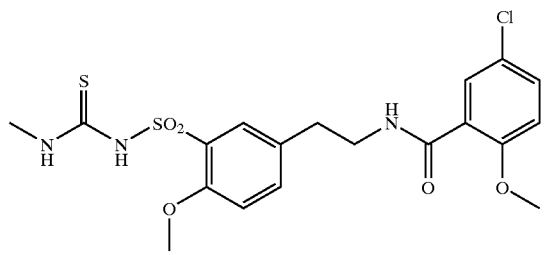

0.40 g (1.0 mmol) of 2-methoxy-5-chloro-N-[5-(1-sulfonylamino-2-methoxyphenyl)-ethyl]-benzamide from Example 1 is dissolved in 5 ml of dry DMF under argon, and 42 mg of sodium hydride (60% strength dispersion in white oil) are added at 0° C. The cooling bath is removed and the mixture is subsequently stirred at room temperature for 30 minutes. 0.10 g of methyl isothiocyanate is introduced into the solution of the sodium sulfonamide and the mixture is subsequently stirred at room temperature for 5 hours and at 70° C. for 1 hour. After cooling, the reaction mixture in poured onto 50 ml of 0.5 N hydrochloric acid. The product which has precipitated is filtered off with suction and dried. Yield: 96%, melting point: 190–193° C.

EXAMPLE 11

2-Methoxy-5-chloro-N-{5-[1-sulfonylamino-N-(methylaminocarbonyl)-2-ethoxyphenyl]-ethyl}-benzamide

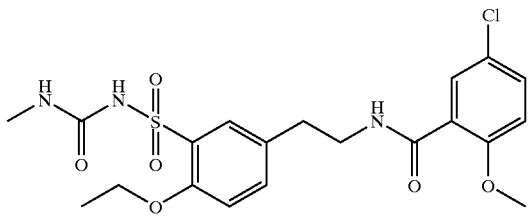

2-Methoxy-5-chloro-N-{5-[1-sulfonylamino-N-(methylaminocarbonyl)-2-ethoxyphenyl]-ethyl}-benzamide is prepared from 4-ethylphenyl-β-ethylamine analogously to Example 1. Melting point: 190–195° C.

EXAMPLE 12

2-Methoxy-5-chloro-N-{5-[1-sulfonylamino-N-(methylaminocarbonyl)-2-ethylphenyl]-ethyl}-benzamide

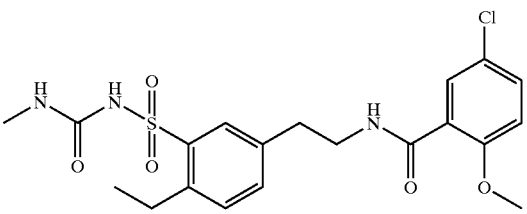

2-Methoxy-5-chloro-N-{5-[1-sulfonylamino-N-(methylaminocarbonyl)-2-ethylphenyl]-ethyl}-benzamide is synthesized from 4-ethylphenyl-β-ethylamine in accordance with Example 1. Melting point: 207° C.

EXAMPLE 13

2-Methoxy-5-chloro-N-{5-[1-sulfonylamino-N-(methylaminocarbonyl)-2-methoxyphenyl]-(3-propyl)}-benzamide

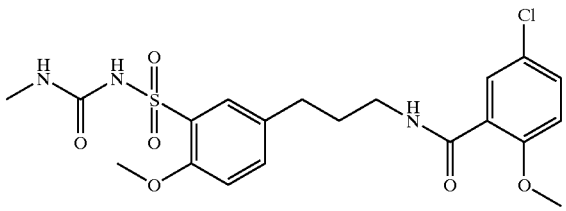

2-Methoxy-5-chloro-N-{5-[1-sulfonylamino-N-(methylaminocarbonyl)-2-methoxyphenyl]-(3-propyl)}-benzamide is synthesized from 4-methoxyphenyl-γ-propylamine analogously to Example 1. Melting point: 285° C.

EXAMPLE 14

2-Methoxy-5-chloro-N-{5-[1-sulfonylamino-N-(methylaminocarbonyl)-2-methoxyphenyl]-(4-butyl)}-benzamide,

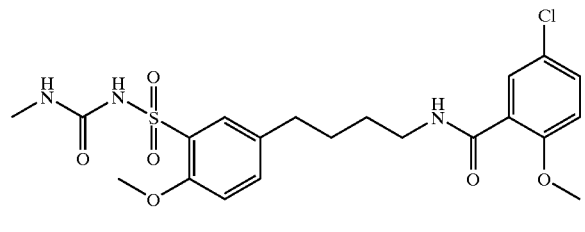

Reaction of 4-methoxyphenyl-δ-butylamine in accordance with Example 1 gives 2-methoxy-5-chloro-N-{5-[1-sulfonylamino-N-(methylaminocarbonyl)-N-methoxyphenyl]-(4-butyl)}-benzamide. The compound has a melting point of 188–190° C.

EXAMPLE 15

2-Methoxy-5-chloro-N-{5-[1-sulfonylamino-N-
(methylaminothiocarbonyl)-2-methylphenyl]-ethyl}-
benzamide,

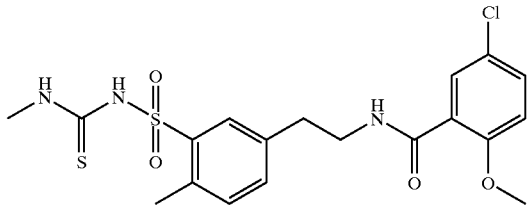

2-Methoxy-5-chloro-N-{5-[1-sulfonylamino-N-
(methylaminothiocarbonyl)-2-methylphenyl]-ethyl}-
benzamide is synthesized analogously to Example 10 from
2-methoxy-5-chloro-N-[5-(1-sulfonylamino-2-
methylphenyl)-ethyl]-benzamide and methyl isothiocyanate. Melting point: 183° C.

EXAMPLE 16

2-Methoxy-5-fluoro-N-{5-[1-sulfonylamino-N-
(methylaminocarbonyl)-2-methoxyphenyl]-ethyl}-
benzamide

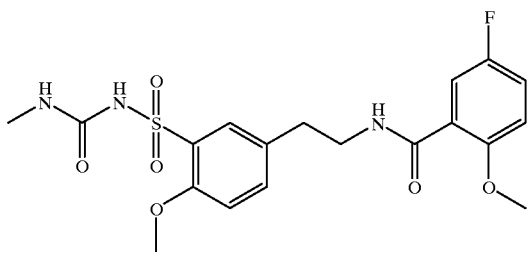

2-Methoxy-5-fluoro-N-{5-[1-sulfonylamino-N-
(methylaminocarbonyl)-2-methoxyphenyl]-ethyl}-
benzamide in synthesized analogously to Example 1. Melting point: 199–200° C.

EXAMPLE 17

2-Methoxy-5-fluoro-N-{5-[1-sulfonylamino-N-
(methylaminothiocarbonyl)-2-methoxyphenyl]-
ethyl}-benzamide

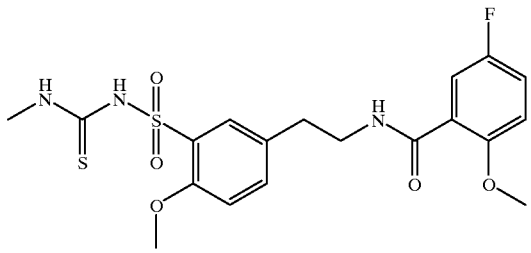

2-Methoxy-5-fluoro-N-{5-[1-sulfonylamino-N-
(methylaminothiocarbonyl)-2-methoxyphenyl]-ethyl}-
benzamide is prepared in accordance with Example 10.
Melting point: 182–185° C.

EXAMPLE 18

2-Methoxy-5-chloro-N-{5-[1-sulfonylamino-N-
(methylaminothiocarbonyl)-2-ethylphenyl]-ethyl}-
benzamide

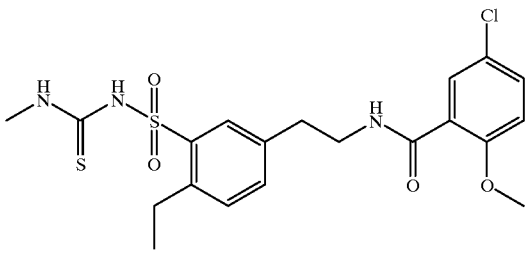

Reaction of 2-methoxy-5-chloro-N-[5-(1-sulfonylamino-2-ethylphenyl)-ethyl]-benzamide and methyl isocyanate in accordance with Example 10 gives 2-methoxy-5-chloro-N-{5-[1-sulfonylamino-N-(methylaminothiocarbonyl)-2-ethylphenyl]-ethyl}-benzamide. Melting point 155° C.

Pharmacological Data:

The therapeutic properties of the compounds I can be demonstrated using the following models:

(1) Action potential duration on the papillary muscle of the guineapig:

(a) introduction

ATP deficiency states such as are observed during ischemia in the cardiac muscle cell lead to a shortening of the duration of action potential. They are one of the causes of so-called reentry arrhythmias, which can cause sudden cardiac death. Opening of ATP-sensitive K channels by the reduction in ATP is a cause of this.

(b) Method

A standard microelectrode technique is used for measurement of the action potential. For this, guineapigs of both sexes are sacrificed by a blow to the head, the hearts are removed and the papillary muscles are separated out and suspended in an organ bath. The organ bath is flushed with Ringer solution (0.9% NaCl, 0.048% KCl, 0.024% $CaCl_2$, 0.02% $NaHCO_3$ and 0.1% glucose) and gassed with a mixture of 95% oxygen and 5% carbon dioxide at a temperature of 36° C. The muscle is stimulated via an electrode with rectangular pulses of 1 V and 1 ms duration and a frequency of 2 Hz. The action potential is conducted and recorded through a glass microelectrode, which is punctured intracellularly and filled with 3 mol KCl solution. The substances to be tested were added to the Ringer solution in a concentration of $2.2 \times 10^{-5}$ mol per liter. The action potential is shown in amplified form on an oscilloscope using a Hugo Sachs amplifier. The duration of the action potential is determined at a repolarization degree of 95% ($APD_{95}$). Shortenings in action potential are caused either by addition of a 1 μM strength solution of the potassium channel opener Hoe 234 (rilmakalim) [W. Linz, E. Klaus, U. Albus, R. H. A. Becker, D. Mania, H. C. Englert, B. A. Schölkens Arzneimittelforechung/Drug Research, Volume 42 (II), 1992, pages 1180–1185] or by addition of 2-deoxyglucose (DEO). ATP deficiency states are caused in experimental physiology by 2-deoxyglucose by blockade of glucose metabolism. The action potential-shortening effect of these substances was prevented or reduced by the simultaneous dose of the test substances. The test substances were added to the bath solution as stock solutions in propanediol. The values stated relate to measurements 30 minutes after the addition. The $APD_{95}$ in the presence of DEO or HOE 234 and in the absence of the test substance serves an a control.

(c) Results:
The following values were measured:

| Measurement | APD$_{95}$-DEO[a] [ms] | APD$_{95}$-HOE 234[a] [ms] |
|---|---|---|
| Control | <40 | <40 |
| Example 1 | 107 ± 14 (155 ± 9) n = 3 | 138 ± 3 (160 ± 20) n = 3 |
| Example 4 | 110 ± 23 (180 ± 5) n = 3 | 123 ± 15 (172 ± 18) n = 3 |
| Example 10 | 125 (175) n = 1 | 137 ± 20 (150 ± 23) n = 3 |

[a]The measurement values from n experiments are followed by the corresponding blank values in parentheses. The blank values are the APD$_{95}$ values at the start of the experiment without DEO, HOE 234 or test substance in the Ringer solution.

(2) Membrane potential on isolated β cells:
(a) Introduction

The action mechanism of hypoglycemic sulfonylureas is clarified in rough outlines. The β cells of the pancreas are the target organ, where increased secretion of the hypoglycemic hormone insulin occurs. The release of insulin is controlled by the cell membrane potential. Glibenclamide causes depolarization of the cell membrane, which promotes insulin release via an increased in-flow of calcium ions. The extent of this depolarization of the call membrane ΔU was determined on RINm5F cells, a pancreas tumor cell line, for some of the compounds according to the invention. The action strength of a compound in this model predicts the extent of the hypoglycemic potential of this compound.

(b) Method
Cell culture of RINm5F cells

RINm5F cells were cultured at 37° C. in RPMI 1640 culture medium (flow), to which 11 mol of glucose, 10% (volume/volume) of fetal calf serum, 2 mmol of glutamine and 50 μg/ml of gentamycin were added. For the studies, the cells were isolated by incubation (about 3 minutes) in a $Ca^{2+}$-free medium containing 0.25% of trypsin and stored on ice.

Measurement method

Isolated RINm5F cells were introduced into a Plexi-glas chamber on an inverse microscope fitted with a differential interference contrast lens. A fire-polished micropipette with an opening diameter of about 1 μm was placed on the cell with the aid of a micromanipulator under optical control (400-fold magnification). By applying a slight reduced pressure in the patch pipette, a high electrical seal was first produced between the glass and cell membrane, and was then broken open by increasing the reduced pressure of the membrane spot under the measurement pipette. The cell potential was recorded in this whole cell configuration with the aid of a patch clamp amplifier (L/M EPC 7) and was measured by applying a potential ramp to the whole cell current.

Solutions: The patch pipette was filled with KCl solution (in mmol): 140 KCl, 10 NaCl, 1.1 $MgCl_2$, 0.5 EGTA, 1 Mg-ATP, 10 HEPES, pH=7.2, and the bath contained NaCl solution (in mmol): 140 NaCl, 4.7 KCl, 1.1 $MgCl_2$, 2 $CaCl_2$, 10 HEPES, pH=7.4.

Stock solutions of the test substances (concentration 100 mmol) in dimethyl sulfoxide (DMSO) and corresponding dilutions in NaCl solution were prepared. DMSO by itself had no effect on the cell potential. In order to stabilize the cell potential under control conditions, the opener for ATP-sensitive $K^+$ channels diazoxide (100 μmol) was added to the bath solution in all the experiments. All the experiments were carried out at 34±1° C.

(c) Results (The concentrations of the compounds according to the invention in the experiments are $10^{-5}$ mol per liter)

| Measurement | ΔU (mv)[a] |
|---|---|
| Example 1 | 13 (−76) n = 6 |
| Example 4 | 19 (−76) n = 3 |
| Example 10 | 11 (−79) n = 3 |

[a]The measurement values from n experiments are followed by the corresponding blank values in parentheses. The blank values are the cell potentials under a dose of diazoxide.

EXAMPLE 19

2-Methoxy-5-chloro-N-{5[-1-sulfonylamino-N-(methylaminothiocarbonyl)-2-chlorophenyl]-ethyl}-benzamide

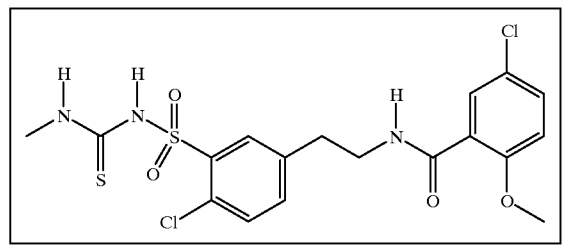

This compound was obtained in accordance with example 10 starting from 2-Methoxy-5-chloro-N-{5-[-1-sulfonylamino-2-chlorophenyl]-ethyl}-benzamide and methyl isothiocyanate. Melting point 194–196° C.

EXAMPLE 20

2-Methoxy-5-chloro-N-{5-[-1-sulfonylamino-N-(methylaminothiocarbonyl)-phenyl]-ethyl}-benzamide

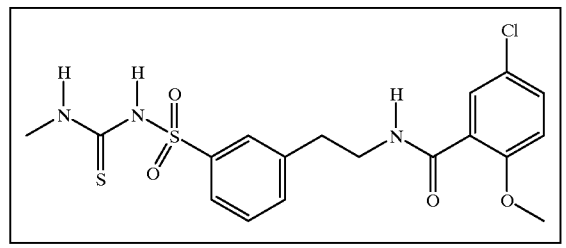

This compound was obtained in accordance with example 10 starting from 2-Methoxy-5-chloro-N-{5-[-1-sulfonylamino-phenyl]-ethyl}-benzemide and methyl isothiocyanat. Melting point 173–175° C.

EXAMPLE 21

2-Methoxy-5-chloro-N-{5-[-1-sulfonylamino-N-(methylaminothiocarbonyl)-2-ethoxyphenyl]-ethyl}-benzamide

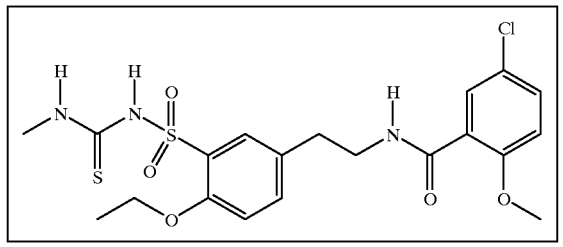

This compound was obtained in accordance with example 10 starting from 2-Methoxy-5-chloro-N-{5-[-1-sulfonylamino-2-ethoxyphenyl]-ethyl}-benzamide and methyl isothiocyanat. Melting point 185–187° C.

EXAMPLE 22

2-Methoxy-5-chloro-N-{5-[-1-sulfonylamino-N-(methylaminothiocarbonyl)-2-(2,2,2-trifluoromethyl)phenyl]-ethyl}-benzamid

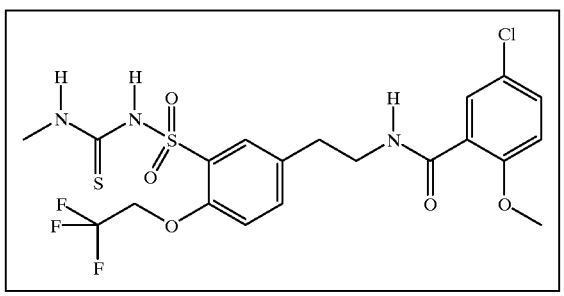

This compound was obtained in accordance with example 10 starting from 2-Methoxy-5-chloro-N-{5-[1-sulfonylamino-2-(2,2,2- trifluoromethyl)phenyl]-ethyl}-benzamide and methyl isothiocyanat. Melting point 167–170° C.

What is claimed is:

1. A process for the preparation of a substituted benzenesulfonylurea or -thiourea of the formula I or of a physiologically acceptable salt thereof,

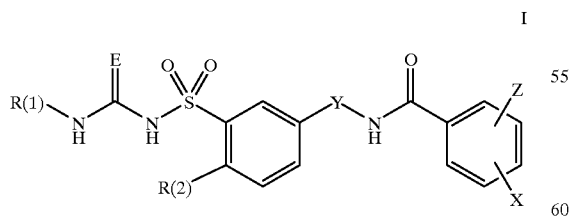

wherein
R(1) is hydrogen or methyl,
R(2) is hydrogen, F, Cl, Br, I, $(C_1-C_6)$-alkyl or $(C_1-C_6)$-alkoxy,
E is oxygen or sulfur,
Y is a hydrocarbon chain of the formula —{CR(3)$_2$}$_n$— where R(3)=H or $(C_1-C_2)$-alkyl and n=1,2,3 or 4,
X is hydrogen, F, Cl, Br, I or $(C_1-C_6)$-alkyl,
Z is F, Cl, Br, I, $NO_2$, $(C_1-C_4)$-alkoxy or $(C_1-C_4)$-alkyl,
comprising
(a) preparing a substituted benzenesulfonylurea of the formula Ia

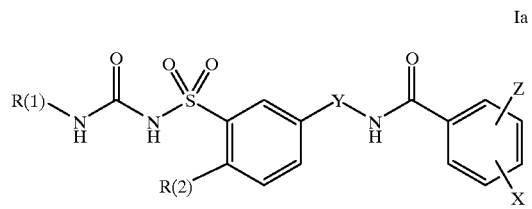

by reacting an aromatic sulfonamide of the formula II or a salt thereof of the formula III,

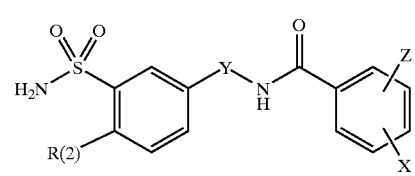

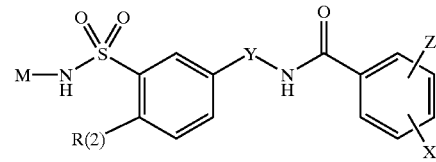

wherein the cation M in the salt of the formula III is an alkali metal or alkaline earth metal ion or a tetraalkylammonium ion, with an R(1)-substituted isocyanate of the formula IV $R(1)\text{-}N\!=\!C\!=\!O$      IV;

or
(b) preparing an unsubstituted benzenesulfonylurea of the formula Ia, wherein R(1) is hydrogen, by reacting an aromatic benzenesulfonamide of the formula II or its salt of the formula III with a trialkylsilyl isocyanate or silicon tetraisocyanate and hydrolysis of the primary silicon-substituted benzenesulfonylurea; or
(c) preparing a benzenesulfonylurea of the formula Ia by reacting an aromatic benzenesulfonamide of the formula II or its salt of the formula III with an R(1)-substituted trichloroacetamide of the formula V

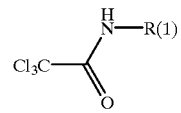

in the absence of a base; or (d) preparing a benzenesulfonylthiourea of the formula Ib

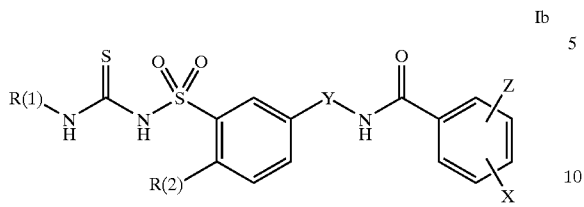

by reacting an aromatic sulfonamide of the formula II or its salt of the formula III with an R(1)-substituted isothiocyanate of the formula VI

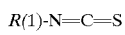

R(1)-N=C=S    VI;

or (e) preparing an unsubstituted benzenesulfonylthiourea of the formula Ib, wherein R(1) is hydrogen, by reacting an aromatic benzenesulfonamide of the formula II or its salt of the formula III with trimethylsilyl isothiocyanate or silicon tetraisothiocyanate and hydrolysis of the silicon-substituted benzenesulfonylthiourea, or by reacting an aromatic benzenesulfonamide of the formula II or its salts of the formula III with benzoyl isothiocyanate and reacting the benzoyl-substituted benzenesulfonylthiourea intermediately formed with aqueous mineral acid;

or (f) preparing a substituted benzenesulfonylurea of the formula Ia by a conversion reaction from the corresponding benzenesulfonylthiourea of the formula Ib;

or (g) preparing a benzenesulfonylurea of the formula Ia by reacting a benzenesulfonyl halide of the formula VII

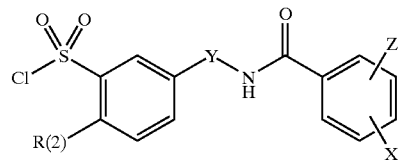

with R(1)-substituted urea or an R(1)-substituted bis(trialkylsilyl)urea and removing the trialkylsilyl protective group;

or (h) preparing a benzenesulfonylurea of the formula Ia by reacting an amine of the formula R(1)-NH$_2$ with a benzenesulfonyl isocyanate of the formula VIII

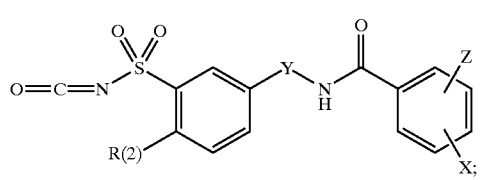

or (i) preparing a benzenesulfonylthiourea of the formula Ib by reacting an amine of the formula R(1)-NH$_2$ with a benzenesulfonylisothiocyanate of the formula IX

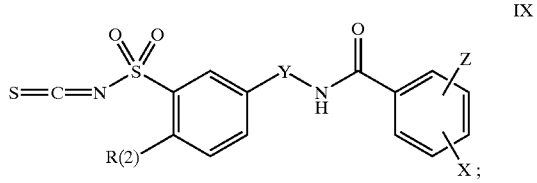

or (j) preparing a substituted benzenesulfonylurea of the formula Ia by oxidizing a correspondingly substituted benzenesulfenyl- or benzenesulfinylurea.

2. The process as claimed in claim 1, wherein
R(1) is hydrogen or methyl,
R(2) is hydrogen, (C$_1$–C$_6$)-alkyl, (C$_1$–C$_6$)-alkoxy, F, Cl, Br or I,
E is oxygen or sulfur,
Y is a hydrocarbon chain of the formula

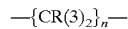

—{CR(3)$_2$}$_n$— where R(3)=H or (C$_1$–C$_2$)-alkyl and n=1,2,3 or 4,
X is hydrogen, F, Cl or (C$_1$–C$_4$)-alkyl,
Z is NO$_2$, F, Cl, (C$_1$–C$_4$)-alkyl or (C$_1$–C$_4$)-alkoxy.

3. The process as claimed in claim 1, wherein
R(1) is hydrogen or methyl,
R(2) is hydrogen, F or Cl,
E is oxygen or sulfur,
Y is a hydrocarbon chain of the formula

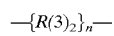

—{R(3)$_2$}$_n$— where R(3)=H or (C$_1$–C$_2$)-alkyl and n=1,2,3 or 4,
X is hydrogen, F, Cl or (C$_1$–C$_4$)-alkyl,
Z is Cl, F, (C$_1$–C$_4$)-alkyl or (C$_1$–C$_4$)-alkoxy.

4. The process as claimed in claim 1, wherein
R(1) is hydrogen or methyl,
R(2) is methoxy or methyl,
E is oxygen or sulfur,
Y is a substituted or unsubstituted hydrocarbon radical having two to three carbon atoms of the formula

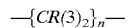

—{CR(3)$_2$}$_n$— where R(3)=H or methyl and n=2 or 3,
X is hydrogen, F, Cl or (C$_1$–C$_3$)-alkyl,
Z is Cl, F, (C$_1$–C$_3$)-alkyl or (C$_1$–C$_3$)-alkoxy.

5. The process as claimed in claim 1, wherein
R(1) is methyl,
R(2) is methoxy or methyl,
E is sulfur,
Y is a substituted or unsubstituted hydrocarbon radical having two to three carbon atoms of the formula

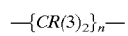

—{CR(3)$_2$}$_n$— where R(3)=H or methyl and n=2 or 3,
X is hydrogen, F, Cl or (C$_1$–C$_3$)-alkyl,
Z is Cl, F, (C$_1$–C$_3$)-alkyl or (C$_1$–C$_3$)-alkoxy,
and wherein the preparation of the benzenesulfonylthiourea of the formula Ib comprises reacting an aromatic sulfonamide of the formula II or a salt thereof of the formula III with an R(1)-substituted isothiocyanate of the formula VI $$R(1)-N=C=S \qquad \text{IV.}$$

6. A process for the preparation of the compound of the formula Ic or of a physiologically acceptable salt thereof,

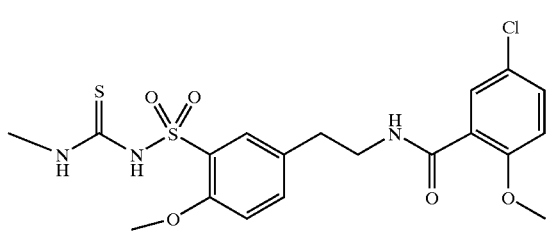

Ic comprising reacting an aromatic sulfonamide of the formula IIa or a salt thereof of the formula IIIa,

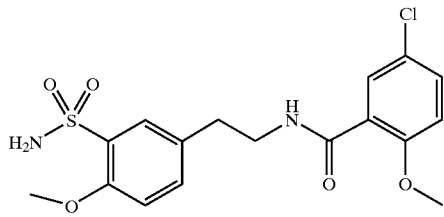

IIa

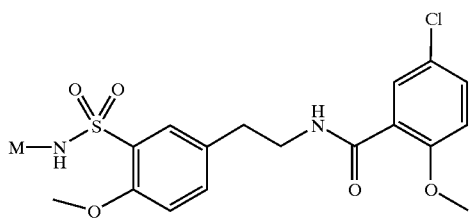

IIIa wherein the cation M in the salt of the formula III is an alkali metal or alkaline earth metal ion or a tetraalkylammonium ion, with methyl isothiocyanate of the formula $CH_3-N=C=S$.

7. The process as claimed in claim 6, wherein a salt of the formula IIIa is reacted with methyl isothiocyanate.

8. A compound of the formula VII,

VII wherein
R(2) is hydrogen or methyl,
Y is a hydrocarbon chain of the formula $$-\{CR(3)_2\}_n-$$

where R(3)=H or $(C_1-C_2)$-alkyl and n=1,2,3 or 4,
X is hydrogen, F, Cl, Br, I or $(C_1-C_6)$-alkyl,
Z is F, Cl, Br, I, $NO_2$, $(C_1-C_4)$-alkoxy or $(C_1-C_4)$-alkyl.

9. The compound as claimed in claim 8, wherein
R(2) is hydrogen or methyl,
Y is a hydrocarbon chain of the formula $$-\{CR(3)_2\}_n-$$

where R(3)=H or $(C_1-C_2)$-alkyl and n=1,2,3 or 4,
X is hydrogen, F, Cl or $(C_1-C_4)$-alkyl,
Z is $NO_2$, F, Cl, $(C_1-C_4)$-alkyl or $(C_1-C_4)$-alkoxy.

10. The compound as claimed in claim 8, wherein
R(2) is hydrogen,
Y is a hydrocarbon chain of the formula $$-\{R(3)_2\}_n-$$

where R(3)=H or $(C_1-C_2)$-alkyl and n=1,2,3 or 4,
X is hydrogen, F, Cl or $(C_1-C_4)$-alkyl,
Z is Cl, F, $(C_1-C_4)$-alkyl or $(C_1-C_4)$-alkoxy.

11. The compound as claimed in claim 8, wherein
R(2) is methyl,
Y is a substituted or unsubstituted hydrocarbon radical having two to three carbon atoms of the formula $$-\{CR(3)_2\}_n-$$

where R(3)=H or methyl and n=2 or 3,
X is hydrogen, F, Cl or $(C_1-C_3)$-alkyl,
Z is Cl, F, $(C_1-C_3)$-alkyl or $(C_1-C_3)$-alkyl or $(C_1-C_3)$-alkoxy.

* * * * *